United States Patent [19]

Toth et al.

[11] Patent Number: 4,774,180

[45] Date of Patent: Sep. 27, 1988

[54] CONSTRUCTION AND APPLICATION OF POLYPROTEINS

[75] Inventors: Matthew J. Toth, Cambridge; Paul R. Schimmel, Lexington, both of Mass.

[73] Assignee: Massachusetts Institute of Technology, Cambridge, Mass.

[21] Appl. No.: 833,920

[22] Filed: Feb. 26, 1986

[51] Int. Cl.[4] .................. C12P 21/00; C12P 21/02; C12N 15/00; C07H 15/12
[52] U.S. Cl. .................................. 435/68; 435/70; 435/172.3; 935/29; 935/47; 536/27
[58] Field of Search .................. 435/68, 70, 172.3; 536/27; 530/350; 935/47

[56] References Cited

U.S. PATENT DOCUMENTS

| | | | |
|---|---|---|---|
| 4,356,270 | 10/1982 | Itakura | 435/317 |
| 4,411,994 | 10/1983 | Gilbert et al. | 435/71 |
| 4,559,300 | 12/1985 | Kovacevic et al. | 435/68 |
| 4,624,926 | 11/1986 | Inouye et al. | 435/253 |

OTHER PUBLICATIONS

Skern et al., *Nucl. Acids Res.*, 13(6): pp. 2111–2126, 1985 (Mar.).
Hanecak et al., *Cell*, 37: pp. 1063–1073, 1984.
Guarente et al., *Science*, 209: pp. 1428–1430, 1980.
"Deletion of an Essential Gene in *Escherichia coli* by Site-Specific Recombination with Linear DNA Fragments", Jasin et al., *Journal of Bacteriology*, (Aug. 1984), pp. 783–786, vol. 159(2).

*Primary Examiner*—Thomas G. Wiseman
*Assistant Examiner*—Thomas D. Mays
*Attorney, Agent, or Firm*—Kilpatrick & Cody

[57] ABSTRACT

A method for constructing polyproteins which can perform multiple sequential activities. A DNA sequence is constructed using genetic engineering techniques to insert sequences encoding the desired proteins into a plasmid, in the correct order, following a single promoter element and before a single stop codon. The reading frames of the mRNA sequences are phased so that a polyprotein with the desired activities, in the required order, is produced.

Modified polyproteins can be produced by inserting or substituting amino acids into the mRNA sequence to create spaces between the individual proteins, to increase the stability of the total polyprotein, to change the spatial orientation of the individual proteins relative to each other and their substrates, and to modify the activity of the individual proteins.

7 Claims, No Drawings

CONSTRUCTION AND APPLICATION OF POLYPROTEINS

BACKGROUND OF THE INVENTION

The United States Government has certain rights in this invention by virture of National Institute of Health Grant No. SR04-GM23562-09.

Many proteins have specialized biological activities. These activities include catalyzing specific reactions and interacting with specific molecules, including ligands, cell surface receptors and other macromolecules. For many applications, it is necessary to combine the activities of two or more proteins to achieve the desired result. For example, a reaction may proceed in multiple steps where the sequential action of two or more enzymes is required to catalyze the overall reaction. In nature, cells which do not produce all of the proteins with the required activity are unable to exist without supplementation with either the protein with the desired activity or the end product of the sequential reaction. Supplementation with the missing or deficient protein first requires isolating the protein with the required activity and, secondly, combining the isolated protein with the substrate at the proper time in the reaction so that the entire sequential reaction can proceed. This is time consuming, laborious and costly. It would be more desirable to have a single protein which could perform the entire reaction.

Polypeptide fusions have been reported in earlier work. The most common example is that of joining an enzyme, such as beta-galactosidase, to a protein to "tag" the protein. The enzyme element is relatively easy to identify using, for example, a spectrophotometric assay, while the protein piece is generally more difficult to measure. There is no connection between the activity, if any, of the protein and the enzyme label and, in general, there is no attempt made to determine whether the protein retains its original activity after it is joined to the enzyme.

There are examples in nature where, in a particular organism, enzymes which sequentially operate in a reaction are joined together. One example is the fatty acid synthetase system, in *E. coli*, consisting of a single polypeptide with multiple activities. The comparable synthetase system in yeast consists of individual proteins.

There are many reasons why proteins usually exist in nature as separate molecules rather than being joined together. The necessity for the protein retaining the proper spatial relationship for binding to a receptor or substrate is one consideration. Another is the inherent instability of large proteins. In one group of proteins, the twenty *E. coli* aminoacyl tRNA synthetases, only two exist as other than a single polypeptide chain. The other two, glycine and phenylalanine, consist of two polypeptides chains. In glycine tRNA synthetase, one chain is responsible for the activation of glycine with ATP to form glycyl-adenylate. The other chain reacts the glycyladenylate with tRNA$^{Gly}$ to yield Gly-tRNA$^{Gly}$. Neither reaction occurs in the absence of the other chain suggesting that the two chains must interact with each other and the tRNA$^{Gly}$.

Heretofore, no one has joined active proteins in such a manner that they not only retain their original activity but can be used to perform sequential reactions. One problem with fusing the proteins together involved changes in the way they can interact together in solution. For example, in glycine tRNA synthetase, joining the two chains, alpha and beta, could prevent the required interaction between the chains unless a means for controlling the spacing and spatial relationship between the two chains was provided. Further, a means for stabilizing the protein in the presence of proteolytic enzymes is required. In their native configuration, areas susceptible to enzymatic degradation are protected by the folding of the protein into a specific three-dimensional structure. Another problem is to provide a means for controlling the spacing along the length of the individual proteins to provide for "channeling" or passing of the reaction products to the appropriate points along the protein chains.

It is therefore an object of the present invention to provide a method for constructing a polyprotein which can perform multiple, sequential activities, in vivo or in vitro.

It is a still further object of the invention to provide a method whereby a protein which can perform multiple, sequential activities can be reproducibly replicated in vivo or in vitro.

It is still another object of the invention to provide a method for modifying polyproteins with multiple biological activites, with respect to their biological activities, their spacial configuration, and the interrelationship of the portions with biological activities.

SUMMARY OF THE INVENTION

A method for constructing and modifying polyproteins which can perform multiple, sequential activities. A polyprotein encoding DNA sequence is constructed using genetic engineering techniques to insert into a plasmid, sequences encoding the desired proteins, in the correct order, following a single promoter element and before a single stop codon. The reading frames of the mRNA sequences are phased to produce a polyprotein with all of the biological activities of the individual proteins. The polyproteins can be modified by insertion or substitution of amino acids to create spaces between the proteins, to increase the stability of the polyprotein, to change the spatial orientation of the individual proteins relative to each other and their substrates, and to modify the biological activities of the individual proteins.

In a specific example, a polyprotein is made from a DNA sequence encoding both a first polypeptide which activates glycine with ATP to form glycyl-adenylate and a second polypeptide which reacts glycyl-adenylate with tRNA$^{Gly}$. The fused DNA sequences are produced with both the DNA encoding the Met initiation site and the DNA sequence encoding a ribosome binding site at the beginning of the second polypeptide deleted so that only the complete polyprotein is produced. The polyprotein is stable with respect to both catalytic activity and molecular weight over time at 37° C.

DETAILED DESCRIPTION OF THE INVENTION

The present invention is a method for constructing "polyproteins", proteins made up of individual proteins that have been joined together in a sequence whereby they retain their original biological activities and ability to interact with each other to perform multi-step reactions, in the proper sequential order.

"Biological activity" includes enzymatic activity, interaction with a receptor, ligand, antigen, or cofactor, phosphorylation, acylation or formation of other modified forms of a compound, and other biological activities known to those skilled in the art.

The polyprotein-encoding DNA sequence is formed by linking or "fusing" sequences encoding each of the individual proteins. The first sequence in the polyprotein DNA construction has a promoter element and a ribosome binding site. These elements assure that transcription of the polyprotein DNA into mRNA begins at a defined site and that the signal, the ribosome binding site, needed for translation of mRNA into protein is present. Synthesis of the polyprotein is made continuous from one protein component to the next by removing or altering any initiation or binding signals and stop codons from the subsequent protein-encoding sequences. The stop codon, normally a signal for the ribosome to stop translation and to end the polypeptide, is not altered or removed from the last DNA sequence. The individual protein encoding sequences are joined such that a proper phasing is made of the mRNA reading frames for translations of the sequence into the desired amino acids.

The primary advantage of the present invention is that a single polyprotein with multiple activities is produced. Another advantage is that the method affords the opportunity to build polyproteins which facilitate "channeling", or the direct passage of the product of one protein, such as an enzyme, to another protein, such as a second enzyme, without passage of the intermediate compound into the solution. Channeling provides a means to sequester and act quickly on highly unstable intermediate compounds which might decay rapidly in free solution.

Once a DNA sequence encoding a polyprotein or a "polyprotein gene" is made, it is necessary to demonstrate that the construction leads to production of a stable polyprotein. If the resulting protein is not stable, for example because the junctions between the proteins are vulnerable to proteolytic digestion, then the junction regions are modified. This can be done by inserting different amino acids at or near the junction or by building spacers of amino acids between the individual proteins. Linkers or spacers can also be introduced to modify the overall activity of the polyprotein. By adjusting the space between and orientation of the individual proteins, it is possible to modify the total activity of the polyprotein.

In one example of the present invention, a single polyprotein was formed by the fusion of the alpha and beta chains of the E. coli glycine tRNA synthetase. The objective was to make a polyprotein which could catalyze a two step reaction. Step one of the reaction is to activate glycine with ATP to form glycyl-adenylate. The second step is to react glycyl-adenylate with tRNA$^{Gly}$ to form Gly-tRNA$^{Gly}$. The entire aminoacylation reaction is written as glycine+ATP+tRNA$^{Gly}$→Gly-tRNA$^{Gly}$+AMP+PPi.

The presence and interaction of both the alpha and beta chains of the glycine tRNA synthetase are required for catalysis of the overall reaction. Neither glycine dependent ATP-PPi exchange nor aminoacylation can be detected with either of the chains alone. Both reactions are detected when the chains are mixed together to generate a complex comprised of two alpha and two beta chains.

In the E. coli genome, the alpha and beta subunits are encoded by a single gene. There is a promoter region, a ribosome binding site, the alpha subunit polypeptide coding region, a stop codon followed by nine nucleotides, the beta subunit coding region, and a stop codon. There is also a separate ribosome binding site for the beta chain, so that synthesis of this chain can proceed independently of synthesis of the alpha chain.

Using genetic engineering techniques known to those skilled in the art, the alpha and beta protein coding regions were fused together to construct one continuous coding sequence within a plasmid. The translation termination signal at the end of the sequence encoding the alpha subunit was altered, as was the translation initiation site at the beginning of the sequence encoding the beta subunit. A linker of six amino acids was inserted to join the end of the coding region of the alpha chain to what is the normal beginning of the beta chain. In the linker region, several different amino acid sequences were tested for their effect on catalytic activity and stability. These sequences generally differed from each other by a single amino acid.

A two-protein polyprotein was synthesized in E. coli and found to be stable both in vivo and in vitro. Most significantly, the fused protein executes the overall two-step reaction with an efficiency that is comparable to that found for the individual proteins, establishing that fusing the two proteins as described does not significantly attenuate the biological activities while affording all of the advantages of a single polypeptide chain. The fused polyprotein functions in vivo as the sole source of glycine tRNA synthetase activity. This is a rigorous test of the efficacy of the fused polyprotein since glycine tRNA synthetase activity is essential for cell growth and any defects or loss of function would cause the cells to die.

The details of the construction of the fused polyproteins and method for analysis are as follows.

In the first step, the gene for the protein or proteins of interest is deleted from the chromosome. In this example, the gene for glycine tRNA synthetase, the glyS locus, was deleted from the E. coli chromosome by a variation of the method in U.S. patent application Ser. No. 688,612 filed Jan. 3, 1985 by Jasin and Schimmel, entitled "A Method for Deletion of An Essential Gene from a Bacteria" for deleting an essential gene from E. coli. The procedure is based upon site specific recombination with a linear DNA fragment that replaces the target gene, in this case glyS, with a Kan$^r$u marker that is bounded by glyS 5' and 3' adjoining sequences. This recombination is done in E. coli JC7623(recBC sbcB) where recBC sbcB mutations inactivate exonucleases that degrade linear DNA fragments. When the chromosomal copy of glyS is deleted to give the delta glyS strain TM10, cell viability is maintained with plasmid pMT 901. Plasmid pMT 901 encodes a HindIII fragment that contains glyS cloned into the HindIII site of plasmid pMT 101. Plasmid pMT 101, encoding Cm$^R$ and Tc$^R$ and a temperature-sensitive replicon such that plasmid replication is blocked at the restrictive temperature (42°), is constructed by inserting the Cm$^R$ locus from pBR 325 into pPM 103, which encodes Tc$^R$ and a temperature-sensitive replicon.

Cell viability is maintained by a plasmid (pMT 901) that encodes glyS and a temperature sensitive replicon. By virtue of the temperature sensitive replicon, plasmid replication is blocked at the restrictive temperature of 42° C. Cell survival therefore depends entirely on the ability of a second plasmid to complement the glyS null allele. This second plasmid is introduced by transformation at the permissive temperature and retained at the temperature that is restrictive for the temperature-sensitive plasmid. The second plasmid contains the specific glyS sequences to be tested.

Functional recA activity is required for the site specific recombination of linear DNA fragments. In the example described by Jasin and Schimmel in U.S. Serial No. 688,612 filed January 3, 1985, also described in "Deletion of an Essential Gene in *Escherichia coli* by Site-Specific Recombination with Linear DNA Fragments" in *J. of Bacteriology*, 159(2), 783-786 (1984), for deletion of alaS, the close proximity of recA to alaS was taken advantage of. A linear DNA fragment was selected that simultaneously deleted alaS and a segment of recA. The resulting recA phenotype thus prevented subsequent recombination of the alaS-maintaining plasmid with the chromosome. In general, recA is required to prevent recombination between plasmid-borne sequences and the chromosome.

In the present example, it was not possible to inactivate recA simultaneously with the deletion of glyS. A two-step procedure was required in which the glyS deletion in TM101/MT901 was first created and the recA 56 allele in *E. coli* GW554 moved into this strain by P1 transduction. The resulting temperature-sensitive delta glyS recA strain is designated TM 102/pMT 901. For reasons of convenience, the delta glyS and recA alleles were then moved into a wild-type *E. coli* C600 strain to produce the temperature-sensitive TM 202/pMT 901 strain.

The glyS deletion in TM 101/pMT 901 was created as follows. Plasmid pTK 101 contains a 10 kbp PstI fragment which encompasses glyS and several kbp of 5'- and 3'-adjoining sequences. The central 5 kbp HindIII fragment of the PstI segment encoding glyS was replaced with a 3.3 kbp HindIII fragment encoding Kan$^r$ from bacterial transposon Tn5. One microgram of the resulting plasmid, pMT300, was digested with EcoRI and NdeI at unique sites in the pBR322 portion of pMT300, and transformed into *E. coli* JC7623/pMT901. Selection for Kan$^r$ yielded approximately 70 transformants. These transformants were presumed to have the delta glyS/Kan$^r$ allele and one of them was designated as TM101/pMT901.

The recA56 allele was moved by P1 transduction into TM101/pMT901to produce TM102/pMT901. Subsequently, both delta glyS and recA56 alleles were moved by P1 transduction from TM102/pM901to a wild-type C600 strain to produce the delta glyS/Kan$^r$ recA strain TM202/pM901. Linkage of Kan$^r$ to xyl-5 in this strain was shown to be similar (90%) to that reported for linkage of glyS to xyl(80%). The genomic arrangement predicted for delta glyS Kan$^r$ was also verified by Southern blot analysis.

Oligonucleotides for insertion into the fixed polypeptide DNA sequence were formed by oligonucleotide-directed mutagenesis using the procedure of M. Zoller and M. Smith in *Methods in Enzymology* 100, 468-500 (1983), as modified by L. Marsh in a personal communication. In this procedure, an oligonucleotide hybridizes to a specific complementary region of a single-stranded DNA template. The oligonucleotide has one or more mismatches with the region of single-stranded DNA to which it hybridizes. As a result, extension of the primer by DNA synthesis with the Klenow fragment of DNA polymerase results in a heteroduplex product. Replication and segregation of the heteroduplex results in mutant and wild-type double-stranded molecules. If the mutant clone does not produce a recognizable phenotype, it may be distinguished from the wild-type clone by its selective hybridization to [$^{32}$P]-labeled "mutagenic" oligonucleotide. The single-stranded DNA of the desired mutant clone hybridizes more strongly to the mutagenic oligonucleotide because of the perfect sequence complementation.

For oligonucleotide-directed mutagenesis, the 5 kbp HindIII fragment that contains the glyS gene was cloned into the single-stranded DNA phage mp8. The initial oligonucleotide-directed mutagenesis used the permutated heptadecamer CCGCCTCTTGCTTATCT. Except for the permuted positions, this oligonucleotide is complementary to the coding strand of glyS that encodes the alpha-subunit stop codon and its 5'- and 3'-flanking sequences, AGATAAGTAAGAGGCGG. The permuted positions alter the TTA that is complementary to the TAA stop, whose position is underlined above.

This oligonucleotide and others were made by phosphoamidite chemistry on a Systec Microsyn 1450A Automatic DNA Synthesizer. The oligonucleotides were purified by denaturing polyacrylamide gel electrophoresis in 8M urea on 20% polyacrylamide gels or by HPLC purification on a reverse phase C-18 column using triethylammonium acetate buffer and an acetonitrile gradient, as recommended by the Systec manual.

Mutant mp8 plaques were detected at a frequency of 16% by hybridization with the 5'-[$^{32}$P]-labeled mutagenic oligonucleotide. Dideoxy sequencing, as modified for alpha-[35S]dATP, with an oligonucleotide that primes close to the site of modification confirmed the putative mutant sequence. Two mutants referred to as Fusion 1 and Fusion 2, were recovered where the TAA stop codon of the alpha subunit was replaced by glutamic acid and glutamine, respectively.

The double-stranded DNA from these mutant mp8 clones was subcloned into the HindIII site of pBR322. The resulting plasmids are glyS fusion-encoding pFN101 (containing Fusion 1) and pFN201 (containing Fusion 2).

A second round of oligonucleotide-directed mutagenesis was performed essentially as described above on the pFN101 and pFN201 glyS fusions. In this procedure, two oligonucleotides TTTCTCTTCTGCAGCCGCCTC and TTTCTCAGCTGCAGCCTC, that are complementary to the coding region were used to eliminate the ATG (complementary to CAT) codon of the beta subunit. (The underline designates the site that was changed.) This was accomplished by a CAT to TGC change which results in a coding strand change of Met to Ala. An AGA to AGC or AGA to TTC change was introduced adjacent to the Met to Ala change. Mutant yields were similar to those previously obtained, and the putative fusion mutants were sequenced and subcloned. These "second generation" fusion mutants, on plasmid pBR322, are designated as pFN102, pFN202 and pFN203, containing Fusions 3, 4, and 5, respectively.

The sequence of the five Fusions are shown in Table 1.

TABLE 1

Fusion Sequences in the Region Between the Alpha and Beta Subunits

| | | | | | | | | | | |
|---|---|---|---|---|---|---|---|---|---|---|
| Wild Type encodes | GAT Asp | AAG Lys | TAA Stop | GAG Glu | GCG Ala | GCT Ala | ATG F-met | TCT Ser | GAG Glu | AAA Lys |
| Fusion 1 (pFN101) | | | GAA Glu | | | | | | | |
| Fusion 2 (pFN201) | | | CAA Gln | | | | | | | |
| Fusion 3 (pFN102) | | | GAA Glu | | | | | GCA Ala | GCT Ala | |
| Fusion 4 (pFN202) | | | CAA Gln | | | | | GCA Ala | GCT Ala | |
| Fusion 5 (pFN203) | | | CAA Gln | | | | | GCA Ala | GAA Glu | |

All of the fusion sequences complement the deletion strain of glyS (TM202). To visualize the plasmid encoded proteins, the maxicell technique described by Sancar et al. in *J. Bact.* 137, 692–693 (1979) was used to produce [$^{35}$S] fusion and wild-type proteins. The labeled proteins were separated on a Laemmli gel (3% stacking gel, 10% running gel), soaked in Autofluor (National Diagnostics), dried onto filtered paper and exposed to x-ray film. Plasmid encoded proteins were identified at the anticipated molecular weights.

Crude extracts of maxicell preparations from the mutant fusion strains were incubated with extracts of wild-type *E. coli* C600 cells to demonstrate resistance of the fusion proteins to degradation.

For biochemical analysis of the fusion proteins, deletion strains containing fusion mutant or wild-type glyS plasmids were grown to late log phase in 100 ml of LB media. Cells were collected by centrifugation, washed with 0.7% saline, centrifuged, scraped into a chilled mortar and pestle, ground with approximately two packed cell volumes of alumina in 1 ml of grinding buffer (50 mM potassium phosphate pH 7.5, 15 mM 2-mercaptoethanol, 200 microliters PMSF-saturated ethanol per liter). The extract was centrifuged at 1200×g in an Eppendorf centrifuge and the supernatant used for analysis.

Aminoacylation assays were performed at 37° C. as described by A. A. Schreier and P. R. Schimmel in *Biochem.* 11, 1582–1589 (1972). Pyrophosphate exchange assays were performed as described by R. Calendar and P. Berg in Procedures in Nucleic Acid Research, G. L. Cantoni and D. R. Davies, eds., pp. 384–399 (1966) as modified by Putney et al. in *J. Biol. Chem.* 256, 198–204 (1981). Beta-lactamase activity of crude extracts was determined spectrophotometrically according to J. A. T. Jansson in *Biochem. Biophys. Acta* 99, 171–172 (1965).

Crude extracts were partially purified by application to an S-300 Sephacryl ™ (Pharmacia Fine Chemica Co.) gel filtration column. A 100 cm×1.1 cm column was packed with superfine Sephacryl ™ S-300 in column buffer, 100 mM NaCl, 1 mM DTT, 10 mM potassium phosphate pH 7.5. The column was calibrated with standard proteins supplied by Boehringer-Mannheim Biochemicals. Flow rates with column buffers were about 7 ml per hour and 1.5 ml fractions were collected. Fractions were assayed for aminoacylation or pyrophosphate exchange.

*E. coli* strains were grown on LB plates or in LB media until stationary phase. M9 minimal media was used in the P1 transduction manipulations. Concentrations of antibiotics, supplied by Sigma Chemical Co., were: Kanamycin, 50 micrograms/ml; chloramphenicol 25 micrograms/ml; ampicillin, 50 micrograms/ml; and tetracycline, 12 micrograms/ml.

All restriction endonucleases were used according to manufacturers specifications. DNA fragments were separated using polyacrylamide gel or agarose gel electrophoresis in a Tris-borate-EDTA buffer using methods known to those skilled in the art.

The efficacy of specific fusion polyproteins was established in vivo in a strain where the chromosomal glyS locus has been deleted as previously discussed.

Table 1 shows the glyS intersubunit region as originally formed by the fusion of the alpha and beta subunit. The translation stop of the alpha-subunit coding region is separated by nine nucleotides from the translation start of the 689 codons of the beta-subunit open reading frame. The intersubunit region encodes a ribosome binding site which enables independent translational initiation at the beginning of the beta-chain. Edman degradation of purified beta-subunit has shown that the mature protein starts with Glu and lacks the Met and Ser that are at the start of the coding region. Oligonucleotide-directed mutagenesis was used initially to construct two simple in-frame fusions of the alpha and beta polypeptides, Fusion 1 and 2. The alpha-chain TAA stop codon was changed to GAA (Glu) in Fusion 1 and to CAA (Gln) in Fusion 2. Each of these fusion constructions on plasmids was transformed into TM202/pM901. There was stable colony growth of the transformants at temperature to 42° C. despite loss of the temperature sensitive plasmid, establishing that the polypeptide per se supports viable cell growth.

To establish the effect of the fusion on the synthesis of the gene product, maxicell analysis of protein products was carried out as described previously. With this procedure, synthesis of plasmid-encoded proteins was visualized by autoradiography of [$^{35}$S]-labeled products that were separated by SDS-gel electrophoresis. The results for Fusion 1 and Fusion 2 show that the fusion proteins are the predominant glyS species in the system. This suggests that the fusion proteins are stable, even though six amino acids have been inserted between the end of the native alpha and the beginning (Glu) of the mature beta chain. Little or no alpha-chain is evident. However, significant amounts of the beta-subunit, in the absence of significant amounts of the alpha chain, suggests that independent initiation of beta-chain synthesis occurred in Fusion 1 and Fusion 2. The independent synthesis of the beta chain was eliminated in Fusions 3, 4, and 5, made by oligonucleotide directed mutagenesis, which were constructed so as to remove the potential for independent ribosome binding at the beginning of the beta subunit coding region.

In Fusions 3, 4, and 5, the beta-chain's methionine initiator codon was replaced with GCA (Ala). This change alone eliminates internal initiation of translation at the start of the beta-piece of the fusion construct. This change was combined with an alteration of the second codon of the beta chain and of the alpha-subunit stop codon TAA.

Fusion 3, 4 and 5 complement the glyS null strain TM202. Maxicell analysis of the translation products clearly shows that stable polyproteins are produced from all three sequences and that neither alpha nor beta chain is produced in significant amounts. This confirms that internal initiation was responsible for the presence of the free beta chain in synthesis from Fusion 1 and Fusion 2. More significantly, complementation of the glyS null strain by the fusion protein, in the absence of significant amounts of either of the free subunits, establishes that the fusion protein itself is active.

The enzymatic activities of extracts of strains bearing Fusions 1–5 were compared with the activity of the wild-type protein. Two activities were measured: the glycine dependent ATP-PPi exchange that monitors aminoacyl adenylate synthesis and the glycine-specific aminoacylation of tRNA. The activities were normalized to the beta-lactamase activity that is also encoded by the multi-copy plasmid containing the fusion sequence to be assayed.

Data given in Table 2 show that, for each of the fusions polyproteins, the glycine-dependent ATP-PPi exchange activity is within 1 to 2 fold of that of the wild-type protein. The aminoacylation activities, while relatively lower, are nonetheless at least 35 to 65% of that of the wild-type enzyme.

TABLE 2
Activity of Wild-Type and Fused Polyprotein Glycine tRNA Synthetase

| Strain | Units of [$^{14}$C]-glycine aminoacylation Activity 1 | Units of AIP-PPi Activity 2 | Units of Beta-lactamase Activity 3 | (Aminoacylation) (Beta-lactamase) | (ATP-PPi) (Beta-lactamase) |
|---|---|---|---|---|---|
| Wild type | 6,250 | 3,318 | 0.170 | 1.0 | 1.0 |
| Fusion 1 | 1,150 | 1,515 | 0.065 | 0.48 | 1.19 |
| Fusion 2 | 430 | 878 | 0.036 | 0.32 | 1.25 |
| Fusion 3 | 900 | 2,303 | 0.055 | 0.45 | 2.15 |
| Fusion 4 | 850 | 1,702 | 0.041 | 0.56 | 2.13 |
| Fusion 5 | 750 | 1,352 | 0.057 | 0.36 | 1.21 |

1. Expressed as the TCA precipitable CPM per minute per microliter of extract
2. Expressed as the charcoal adsorbed [$^{32}$P] CPM per 15 minute assay per microliter of extract
3. Expressed as the absolute change of absorbance at 240 nm per minute per microliter of extract The stability of the Fusion 2 polyprotein over time was also investigated. Maxicell extracts were allowed to incubate for one hour at 37° before electrophoresis. This had no discernible effect on the yield of fusion protein or on the appearance of alpha- or beta-chain products resulting from breakdown of the fusion protein. In another experiment, the activities of Fusion 3 protein were also unchanged at room temperature for at least three hours.

In summary, this example demonstrates that the method of the present invention is useful in constructing polyproteins, and single DNA sequences encoding such polyproteins, which retain the individual biological activities and which can function in a sequential fashion. The example further demonstrates the usefulness of the method of the present invention in modifying these DNA sequences to produce polyproteins with altered spatial relationships, stability, and biological activities.

The present invention may be embodied in other specific forms without departing from the spirit and scope thereof. These and other modifications of the invention will occur to those skilled in the art. Such other embodiments and modifications are intended to fall within the scope of the appended claims.

We claim:

1. A method for constructing polyproteins comprising:
   (a) isolating nucleotide sequences encoding proteins which interact with one another in multi-step sequential enzymatic and binding reactions;
   (b) selecting a vector suitable for the insertion of the nucleotide sequences encoding the proteins;
   (c) inserting the nucleotide sequences isolated in step (a) into the vector of step (b);
   (d) screening for and removing from the inserted sequences any stop codons other than at the end of the last inserted sequence and any ribosome binding sites other than at the beginning of the first protein-encoding sequence; and
   (e) phasing the reading frames of the individual protein encoding sequences so that a single polyprotein with multiple activites is translated from the inserted nucleotide sequences.

2. The method of claim 1 further comprising inserting amino acids in addition to or in place of amino acids in the inserted sequences.

3. The method of claim 1 further comprising removing any initiator codons other than the initiator codon at the beginning of the first inserted sequence.

4. The method of claim 1 further comprising inserting codons encoding selected amino acids adjacent to the protein encoding sequences.

5. The method of claim 4 wherein the amino acids alter the spatial relationship between the proteins.

6. The method of claim 4 wherein the selected amino acids are replaced or removed to produce a junction resistant to proteolytic attack.

7. An engineered DNA sequence comprising codons sequentially encoding a promoter region, a single ribosome binding site, a region encoding a plurality of proteins and a single stop codon, wherein the encoded proteins interact with one another to perform sequential multi-step enzymatic and binding reactions.

* * * * *

UNITED STATES PATENT AND TRADEMARK OFFICE
CERTIFICATE OF CORRECTION

PATENT NO. : 4,774,180

DATED : September 27, 1988

INVENTOR(S) : Matthew J. Toth et al.

Page 1 of 2

It is certified that error appears in the above-identified patent and that said Letters Patent is hereby corrected as shown below:

Title, delete "APPLICATION" and insert --APPLICATIONS--.

Column 1, title, delete "APPLICATION" and insert --APPLICATIONS--.

Column 1, lines 42 and 43, after "reaction" insert --pathway--.

Column 3, line 20, delete "translations" and insert --translation--.

Column 4, line 45, delete "u" before "marker."

Column 4, line 51, delete "TM10" and insert --TM101--.

Column 6, line 16, delete "CCGCCTCTTGCTTATCT" and insert --CCGCCTC<u>TT</u>GCTTATCT--.

Column 6, line 21, delete "AGATAAGTAAGAGGCGG" and insert --AGATAAG<u>TA</u>AGAGGCGG--.

Column 6, line 52, delete "TTTCTCTTCTGCAGCCGCCTC" and insert --TTTCTCTTC<u>TG</u>CAGCCGCCTC--.

Column 6, line 53, delete "TTTCTCAGCTGCAGCCTC" and insert --TTTCTCAGC<u>TG</u>CAGCCTC--.

Column 7, line 40, delete "1200" and insert --12000--.

UNITED STATES PATENT AND TRADEMARK OFFICE
CERTIFICATE OF CORRECTION

PATENT NO. : 4,774,180

DATED : September 27, 1988

INVENTOR(S) : Matthew J. Toth et al.

It is certified that error appears in the above-identified patent and that said Letters Patent is hereby corrected as shown below:

Column 9, Table 2, heading of third column, delete "AIP-PPi" and insert --ATP-PPi--.

Signed and Sealed this

Fourteenth Day of November, 1989

*Attest:*

JEFFREY M. SAMUELS

*Attesting Officer*     *Acting Commissioner of Patents and Trademarks*